United States Patent
Kersting

(10) Patent No.: US 7,915,588 B2
(45) Date of Patent: Mar. 29, 2011

(54) ARRANGEMENT AND METHOD FOR DETECTING AN OBJECT WHICH IS ARRANGED ON A BODY, IN PARTICULAR FOR CARRYING OUT A SECURITY CHECK

(75) Inventor: Roland Kersting, Munich (DE)

(73) Assignee: Ludwig-Maximilians-Universitaet Muenchen, Munich (DE)

( * ) Notice: Subject to any disclaimer, the term of this patent is extended or adjusted under 35 U.S.C. 154(b) by 158 days.

(21) Appl. No.: 12/446,162

(22) PCT Filed: Oct. 17, 2007

(86) PCT No.: PCT/EP2007/009000
§ 371 (c)(1),
(2), (4) Date: Apr. 17, 2009

(87) PCT Pub. No.: WO2008/046604
PCT Pub. Date: Apr. 24, 2008

(65) Prior Publication Data
US 2010/0288930 A1 Nov. 18, 2010

(30) Foreign Application Priority Data

Oct. 18, 2006 (DE) .......................... 10 2006 049 152

(51) Int. Cl.
*G01J 5/02* (2006.01)
(52) U.S. Cl. .................................................. 250/341.1
(58) Field of Classification Search ..... 250/341.1–341.8
See application file for complete search history.

(56) References Cited

U.S. PATENT DOCUMENTS

| 7,365,672 B2 * | 4/2008 | Keller et al. ..................... 342/22 |
| 7,549,339 B2 * | 6/2009 | Staroselsky et al. ............ 73/601 |
| 2005/0231421 A1 | 10/2005 | Fleisher et al. |

(Continued)

FOREIGN PATENT DOCUMENTS

DE     195 02 756     8/1996

(Continued)

OTHER PUBLICATIONS

Buersgens et al., "Acoustic Phase Imaging with Teraherz Radiation," Optics Express, vol. 15, No. 8, pp. 4427-4434, XP002465898 (Apr. 3, 2007).

(Continued)

*Primary Examiner* — David P Porta
*Assistant Examiner* — Kiho Kim
(74) *Attorney, Agent, or Firm* — Greenblum & Bernstein, P.L.C.

(57) ABSTRACT

The invention relates to an arrangement (10) and a method for detecting an object (18) arranged on a body (14). The arrangement comprises a vibration device (12), which sets the body (14) in a mechanical vibration of predetermined vibration frequency and predetermined vibration phase, an emission device (20) which emits in the direction of the body (14) a coherent electromagnetic detection radiation (26), the radiation frequency of which is selected such that it is reflected at least in part by the body (14) and the object (18) to be detected, a receiver device (30), which receives the radiation (28) reflected by the body (14) and the object (18), and an evaluation device (32) which filters out of the radiation (28) received the portions having the predetermined vibration frequency and evaluates them with respect to their vibration phase difference from the predetermined vibration phase.

19 Claims, 1 Drawing Sheet

U.S. PATENT DOCUMENTS

2006/0214107 A1 9/2006 Mueller

FOREIGN PATENT DOCUMENTS

| | | |
|---|---|---|
| DE | 10 2005 053 656 | 5/2007 |
| EP | 07 69 698 | 6/1996 |
| EP | 09 32 050 | 12/1998 |
| EP | 14 31 740 | 12/2002 |

OTHER PUBLICATIONS

Buersgens et al., "Millimeter Wave Probing of the Acoustic Phase for Concealed Object Detection," Optics Express, vol. 15, No. 14, pp. 8838-8843, XP002465899 (Jul. 2, 2007).

Wang et al., "Phase Signatures in Acoustic-Seismic Landmine Detection," Proc. SPIE, Bd. 5415, pp. 70-79 (2004).

Hebel et al., "Model-based Mine Verification with Scanning Laser Doppler Vibrometry Data," Proc. SPIE, Bd. 5415, pp. 80-90 (2004).

Ryan et al., "Credibility Assessments: Operation Issues and Technology Impact for Law Enforcement Application," Proc. SPIE, Bd. 5071, pp. 168-182 (2003).

* cited by examiner

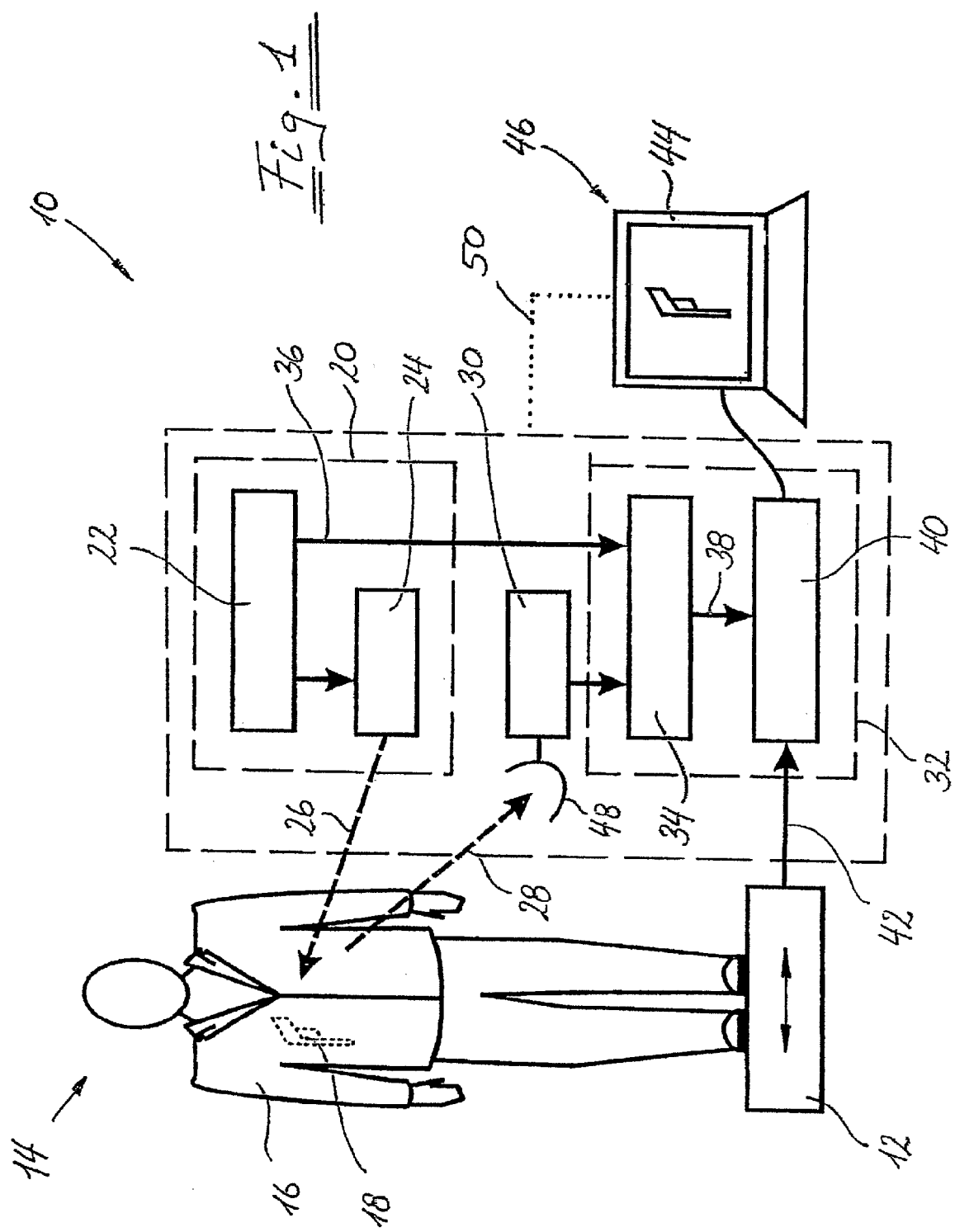

ARRANGEMENT AND METHOD FOR DETECTING AN OBJECT WHICH IS ARRANGED ON A BODY, IN PARTICULAR FOR CARRYING OUT A SECURITY CHECK

CROSS-REFERENCE TO RELATED APPLICATIONS

The present application is a U.S. National Stage of International Patent Application No. PCT/EP2007/009000 filed Oct. 17, 2007 and claims priority under 35 U.S.C. §119 of German Patent Application No. 10 2006 049 152.1 filed Oct. 18, 2006. Moreover, the disclosure of International Patent Application No. PCT/EP2007/009000 is expressly incorporated by reference herein in its entirety.

BACKGROUND OF THE INVENTION

1. Field of the Invention

The invention relates to an arrangement and a method for detecting an object arranged on a body, but possibly concealed by at least one covering material.

2. Discussion of Background Information

Arrangements of this type are generally known. For example, at airports or at large events metal detectors are used for security control, with the aid of which metal weapons can be detected. However, this method fails, for example, with ceramic knives. Furthermore, it is known that with the aid of mass spectrometers the smallest contaminations of explosives can be detected. Finally, it is also known to use specially trained dogs for detecting illegal drugs. All of these methods have the disadvantage in common that they relate only to specific classes of substances. A number of detectors would therefore be necessary to safeguard against all possible dangerous or objectionable objects or materials. In particular for reasons of time, however, the successive use of several technologies of this type in security checks is not practicable. Finally, it is also known to detect concealed objects with the aid of x-rays. However, this method cannot be applied to the human body or only to a very limited extent.

SUMMARY OF THE INVENTION

The invention discloses an arrangement and a method of the type mentioned at the outset, which is able irrespective of specific classes of materials, to detect in a contactless manner whether an object is arranged on a body, and which is also suitable for use on the human body.

According to a first aspect of the invention through an arrangement for detecting an object arranged on a body, the arrangement comprises a vibration device, which sets the body in a mechanical vibration of predetermined vibration frequency and predetermined vibration phase, an emission device, which emits a coherent electromagnetic detection radiation in the direction of the body, the radiation frequency of which is selected such that it is reflected at least in part by the body and the object to be detected, a receiver device, which receives the radiation reflected by the body and the object, and an evaluation device, which filters out of the radiation received the portions having the predetermined vibration frequency and evaluates them with respect to their vibration phase difference from the predetermined vibration phase.

Although the invention is discussed and explained below mainly on the basis of the example of the security check of people, i.e., thus in its application for a human body, it should be noted at this point that the invention is not limited thereto, and can be used just as well for animal bodies and/or inanimate bodies and/or objects.

The invention is based on the realization that with forced vibrations the phase difference between the motion of the object set in forced vibration relative to the exciter vibration, in addition to the mass of the object and its attenuation, among other things also depends on the strength of its coupling to the exciter vibration.

If a person is now set in forced vibration, for example, if he is placed on a vibration plate, the body of the person, in the case in the example starting from the feet, starts to vibrate. Whether this forced vibration of the body thereby means that the entire body vibrates relative to the predetermined vibration phase of the exciter vibration with essentially one and the same phase difference or the different parts of the body vibrate with different phase difference also depends, in addition to the respectively selected type of excitation, on its predetermined vibration frequency. However, in any case the mechanical vibration of a body part on which the object to be detected is arranged, for its part again represents an exciter vibration, which sets the object in a forced mechanical vibration. It is to the credit of the inventor to have recognized that objects carried on the body can be detected due to the phase difference of their forced vibration relative to the phase of the vibration of the body parts on which they are arranged. The invention utilizes this effect:

If the type of the device exciting the body to vibration and the vibration frequency thereof are selected such that the entire body oscillates relative to the predetermined vibration phase of the exciter vibration with essentially one and the same phase difference, it can always be indicated to the staff carrying out the security check when subsections are present in the radiation sections filtered out by the evaluation device and having the predetermined vibration frequency, the phase difference of which subsections from the predetermined vibration phase of the mechanical vibration lies in a predetermined value range, via a visual, acoustic or any type of signal that the person just checked is carrying objects on his body. Based on this display the person checked can then be subjected, for example, to a body search.

It should be emphasized in this connection that the arrangement according to the invention is even able to detect the object if it is covered by at least one covering material, as long as the radiation frequency of the detection radiation is selected such that it is transmitted at least in part by the at least one covering material.

It should be noted that the arrangement according to the invention evaluates portions of the reflected radiation having the predetermined vibration frequency only with respect to their phase position, but not with respect to their amplitude. The percentage of the detection radiation emitted in the direction of the body that is optionally absorbed by the at least one covering material is therefore irrelevant, as long as only the signal-to-noise ratio of the radiation reflected by the objects to be detected permits a detection of this radiation.

And this applies regardless of what type of covering material it is. In the case of security checks of people, at least one covering material can be a typical clothing material, that is a textile material, for example, a natural textile material, such as wool, cotton, linen and the like, or a synthetic textile material, such as polyester, polyamide, nylon and the like, a natural material, such as leather and the like, or a mixture of two or more of the above-referenced materials.

It should be noted that no knowledge of the concealed objects or of their properties, for example, their mechanical properties, is necessary, which means that prior calibration measurements of objects potentially to be detected are unnecessary.

In contrast to radar methods, the transit time of an electromagnetic signal, in the present case of the detection radiation, from the emission device via the object or the body to the receiver device is not measured. Because on the one hand, information provided by transit time measurements of this type, namely the distance of the object from the detection arrangement, is not required, since it is a matter only of detecting the presence of the object to be detected. And on the other hand, the volume of data associated with this information would considerably increase the expenditure in terms of equipment. It should further be taken into consideration that a travel distance difference of 1 mm requires a resolution per time unit of the transit time signal of approx. 3 ps, which would require a correspondingly fast and thus cost-intensive electronic system. In comparison thereto the evaluation of vibration phase differences is considerably more cost-effective.

The terahertz radiation is particularly suitable as detection radiation. This radiation, on the one hand does not have any effects on the human body that are harmful to health, since terahertz photons have an extremely low energy and therefore cannot ionize biological tissue, although terahertz radiation is very strongly absorbed by water. On the other hand, terahertz radiation has the desired reflection or transmission properties. The transmission coefficient of a terahertz radiation of between 0.1 THz and 0.5 THz thus lies in the order of magnitude of 90% for textile materials, such as jeans, cotton socks and linen shirts, and for 0.5 THz in the order of magnitude of 30% for 2 mm thick leather, while for 0.1 THz it is again approx. 90%. Furthermore, the reflection coefficient of skin in the frequency range in question is more than 10%. Moreover, most textiles are characterized in the Thz range by a negligible reflection, whereby they contribute only insignificantly to the determination of the phase position of the reflected radiation, since this originates essentially in the body or the object. Moreover, terahertz radiation of these frequencies has a wavelength that is greater than typical texture sizes of textile materials. Hardly any Mie scattering therefore takes place on the surface of garments.

In this context it should be noted that the above-mentioned frequencies could likewise be referred to as 200 GHz or 500 GHz. However, they are usually still attributed to "terahertz radiation," since they have the same transmission, reflection and absorption properties as this.

Typical Gunn oscillators used to generate terahertz radiation provide an output power of approx. 30 mW. Furthermore, the reflected terahertz radiation can be resolved down to powers of approx. 30 pW. To irradiate the body a power can therefore already be sufficient that lies far below the maximum radiation power permissible for mobile phones of approx. 1 W. This underlines the harmless nature of the application of the arrangement according to the invention within the scope of a security check of people.

It should be mentioned in this context that there are also regulations for mechanical vibrations, which must be observed to avoid harm to the health of people tested. These are set forth, for example, in ISO 2631-1. Thus with a vibration frequency of 100 Hz and a vibration amplitude of 0.1 mm, the maximum permissible vibration duration is 10 minutes. Naturally, this value lies far above the duration tolerable for a security check. It was shown that by means of terahertz technologies vibration amplitudes down to 200 nm can be detected, which lies approximately three orders of magnitude below the vibration amplitude of 0.1 mm. It is further interesting that an amplitude of approx. 1 µm is usually given as a perception threshold and an amplitude of approx. 1 mm is usually given as a pain threshold.

Within the scope of the present invention, for example, mechanical vibrations with a vibration frequency in the range of between approx. 1 Hz and approx. 20,000 Hz, preferably between approx. 50 Hz and approx. 200 Hz, even more preferably approx. 100 Hz, can be used. Even at these frequencies the respectively maximum tolerable duration for the action of mechanical vibration can be substantially undercut, since vibration amplitudes down to 500 nm can be resolved with the arrangement according to the invention.

Although the use of a vibration plate for introducing the mechanical vibrations into the body is preferred, a coupling via loudspeakers or the like can fundamentally also be considered. The coupling of vibrations into the body can also be carried out via a seat or quite generally via other parts of the body.

In order to be able to facilitate the evaluation of the reflected radiation, the evaluation device can comprise a superimposition device, which superimposes a reference radiation on the received reflected radiation, which reference radiation is in a fixed radiation phase relationship to the detection radiation. This reference radiation can be, for example, a portion of the generated detection radiation directly fed by the emission device of the superimposition device. The superimposition of the reference radiation on the reflected radiation can be described as an interference that depends on the difference between the track of the reference radiation on the one hand and the sum of the tracks of the radiation emitted towards the body and reflected thereby on the other hand. To this end, it is necessary only that the coherence length of the detection radiation generated by the emission device is greater than the sum of the tracks of the radiation emitted towards the body and reflected therefrom.

The reference radiation with its predetermined radiation frequency and its predetermined radiation phase position is accordingly used as a tool for scanning the reflected radiation. Of course, however, other methods could also be used for scanning the reflected radiation, similar to those such as are known, for example, from radio frequency technology for scanning radio waves. Time-resolved methods are also possible, in which the vibration of the electromagnetic field is directly detected. Even though these methods have hitherto been available for only a part of the terahertz spectrum, it cannot be ruled out that similar methods will also be developed over the next few years for higher terahertz frequencies.

The actual evaluation or analysis of the reflected or superimposed radiation with respect to its vibration phase difference from the predetermined vibration phase can be carried out with the aid of known techniques. Since the objects to be detected are modulated in their spatial position, in particular modulation techniques can be used to this end, which are characterized by high contrast and low noise, for example the lock-in technique or digital data processing.

In particular for the field of security checks of people, it is desirable to facilitate the evaluation of the result of the examination for the security staff with the aid of an imaging technology. This can also be realized with the aid of terahertz radiation, since its wavelength is smaller than the typical size of the objects to be imaged. An imaging can be provided in a simple manner in that an imaging optical system with spatial resolution is arranged upstream of the receiver device. The term "optical system" in the present case naturally does not relate to visible electromagnetic radiation, but to the terahertz radiation used. The imaging optical system with spatial resolution can be realized, for example, by sequential scanning in two directions, for example, the vertical and a horizontal direction, or through parallel detection methods, in which entire image lines, entire image columns or the entire image are processed in a parallel manner. Methods are also possible which have become known under the catchword "synthetic aperture."

The display of the result of the check can be carried out on an imaging device, for example, a screen. To this end different values can be assigned to different vibration phase differences by means of evaluation algorithms, and these values can be displayed, for example, by a different color. Further measurement data can also be taken into account in the formation of the values. If the exciter vibration is selected such that essentially the entire body oscillates relative to the predetermined vibration phase of the exciter vibration with one and the same phase difference, the predetermined vibration phase can be used as a reference phase in the formation of the vibration phase differences. If the exciter vibration, however, leads to the different parts of the body oscillating with different phase difference, in the determination of the vibration phase difference to be assigned to a specific image area, the phase position of the signal of an image area surrounding the specific image area and/or adjacent thereto can be used as a reference phase.

Fundamentally it would be possible not only to represent the concealed objects on the screen, but also the person examined. However, this would inevitably lead to a representation of the naked body of the person examined, which is not tolerable for ethical reasons. Therefore, in connection with the use of an imaging technology it is also preferred to display a location as a pixel only when the imaging value lies in a predetermined value range. In this manner it can be ensured that only the objects to be detected are displayed. Through this the security staff receive additional information on the object, namely on the one hand information on the location where the object is carried on the body and on the other hand information on the type of object in question from the shape of the image.

It should be added that the operation does not necessarily need to be carried out with a single mechanical vibration of predetermined frequency and predetermined phase position as well as predetermined amplitude and predetermined vibration direction. Instead the fact can be utilized that according to Fourier any arbitrary vibration can be shown by superimposition of a plurality of vibrations of predetermined frequency, predetermined phase position, predetermined amplitude and predetermined vibration direction. The signal analysis according to the invention for each of these Fourier components of the mechanical vibration can therefore be carried out separately.

The same also applies to the detection radiation used: here too instead of a monofrequent signal, a composite signal can also be used, which can be represented as a Fourier sum of monofrequent individual signals.

BRIEF DESCRIPTION OF THE DRAWINGS

The invention is explained in more detail below using an exemplary embodiment based on the attached drawings. It shows:

FIG. 1 diagrammatically illustrates the structure of an arrangement according to the invention.

DETAILED DESCRIPTION OF THE PRESENT INVENTION

FIG. 1 shows a detection arrangement according to the invention labeled generally by 10. It comprises a vibration plate 12, on which the body to be examined, in the present case the person 14 to be examined, is arranged. The person 14 carries concealed beneath his clothing 16 an object 18, in the present case a handgun, and it is the object of the detection arrangement 10 to detect this object 18.

To this end, the vibration plate 12 is set in vibration with a predetermined frequency and a known phase, wherein this vibration as a forced vibration is also transferred to the body of the person 14 together with his clothing 16 and the handgun 18 carried in a concealed manner. The resulting movement of the person 14, the clothing 16 and the concealed object 18 is scanned by means of terahertz radiation.

To this end, the detection arrangement 10 comprises an emission device 20 with a radiation generation device 22 for terahertz radiation, which can contain, for example, a Gunn oscillator, and a transmitter device 24, which emits the terahertz radiation as detection radiation 26 in the direction of the body of the person 14.

The radiation 28 reflected by the body 14 is picked up by a receiver device 30 and fed to an evaluation device 32. Namely, to be more precise, it is fed to a superimposition device 34 of the evaluation device 32, which superimposes a reference radiation 36 on the reflected radiation 28, which reference radiation is in a known radiation phase relationship to the detection radiation 26. In the case shown in FIG. 1, the reference radiation is nothing but a part of the terahertz radiation generated by the emission device 20, to be more exact, the radiation generation device 22 thereof.

Since the reference radiation 36 thus has the same radiation frequency as the reflected radiation 28, and furthermore the coherence length of the terahertz radiation generated by the radiation generation device 22 is greater than the difference of the tracks of detection radiation 26 and reflected radiation 28 on the one hand and the reference radiation 36 on the other hand, the reference radiation 36 is ideally suitable for scanning the phase length of the reflected radiation. Through the superimposition of the reference radiation 36 on the reflected radiation 28, a signal is obtained which depicts the track change of the reflected radiation 28 as a result of the vibration of the body of the person 14, his clothing 16 and the object 18 carried in a concealed manner.

The superimposed signal 38 is then sent to an analysis device 40 of the evaluation device 32, which filters out of the superimposed radiation 38 the portions having the predetermined vibration frequency of the vibration device 12 and analyzes them with respect to their vibration phase difference from the predetermined vibration phase of the mechanical vibration of the vibration device 12. To this end the analysis device 40 receives from the vibration device 12 a reference signal 42, which depicts the frequency and phase of the vibration device 12.

The evaluation device 32, to be more exact, the analysis device 40 thereof, preferably emits a display signal to a display device 44 only when this vibration phase difference lies in a predetermined value range that is typical for the reaction of objects 18 carried in a concealed manner to the vibration of the vibration device 12.

As shown in FIG. 1, the display device 44 can be an imaging display device, for example the screen of a computer 46. In order to be able to render possible a display with spatial resolution on the screen 44, an optical system 48 with spatial resolution is arranged upstream of the receiver device 30, which optical system scans the body of the person 14 in a two-dimensional manner. The spatial resolution can thereby be for example 1 mm$^2$.

In conclusion, it should be noted that the computer 46 can also be used to control the detection arrangement 10, which is shown in FIG. 1 by the dotted line 50.

In a concrete case, with the use of CW (continuous wave) radiation a possibility results of receiving access to the acoustic phase. If the reflected radiation is mixed in the homodyne method with a reference beam, the interference depends on the path differences between the two beams. The extension of the path $(x_2-x_1)$ through the acoustic vibration of the object then leads to a periodic interference signal, which depicts the acoustic phase $(\omega_{acoust}t+\Phi)$ of the object. On the time scale of the acoustic vibrations, after notification about the THz period an interference signal results, wherein $\Delta=x_{2.0}-x_{1.0}$ is the path length difference in neutral position and A is the amplitude of the vibration:

$$\hat{I}(t) = 2\sqrt{I_1 I_2} \cdot \cos\left(\frac{2\pi}{\lambda THz}[\Delta + 2A\sin(\omega_{acoust}t + \phi)]\right) = const \cdot \cos(a + b(t)) \tag{1}$$

With the development of the cosine in a power series and subsequent restriction to terms of the first harmonic of $\omega_{acoust}$, that is, just as it makes a frequency filter, the following results:

$$\cos(a + b(t))|_{\omega_{acoust}} = \left[-a + \frac{1}{6}a^3 - \frac{1}{90}a^5 \pm \ldots\right] \cdot \sin(\omega_{acoust}t + \phi) \tag{2}$$

The last term shows that the acoustic phase results from the interference with the use of a frequency filter. However, the amplitudes converge depending on A against a positive or against a negative value of the same size. It should be noted that this measuring principle permits only two possible results, namely either an acoustic phase of $-\Phi$ or of $+\Phi$. If the object is not driven to oscillate directly, but via a body lying in between with the phase $\Psi$, the two possible measuring values result in $\Psi\pm\Phi$.

If the acoustic phase $\Phi$ deviates from 90°, the measuring principle yields the possible results $\Phi$ or $\Phi-\pi$.

It should also be added that the signal-to-noise ratio of the signal evaluated by the evaluation device 32 to determine the acoustic phase depends on the optical phase with which the detection radiation emitted by the emission device 20 strikes the body 14. However, it is possible to set or optimize the signal-to-noise ratio for each pixel at a high value, namely through changing the wavelength of the detection radiation emitted by the emission device 20 or through changing the position of the emission device 20 or through another suitable measure. It should be taken into consideration thereby that with a wavelength of the detection radiation in the order of magnitude of 1 mm and a distance between emission device and body in the order of magnitude of 1 m a wavelength change in the order of magnitude of 0.1% or a position change in the order of magnitude of 1 mm is already sufficient.

Furthermore, it is possible to avoid undesirable jumps of the acoustic phase between $\Phi$ or $\Psi-\pi$ through the suitable selection of the wavelength of the detection radiation and/or the distance between emission device and body. The signal evaluated for determining the acoustic phase by the evaluation device 32 can hereby be more clearly interpreted and thus more easily evaluated.

With respect to the criteria referenced above, it can be summarized that the discussed technology is a modulation technology and thus a good sensitivity is to be expected, that the technology leads to a sufficiently clear measurement signal, that the criterion of completeness is met, since all objects with a mass can be detected, that the method can be carried out on people in a physiologically tolerable manner, that the method is ethically unobjectionable with respect to the representation of the human body. Due to the clarity of the measurement values, it is easy to represent only those objects that are distinguishable from the background in their acoustic phase.

The invention claimed is:

1. An arrangement for detecting an object arranged on a body, comprising:
a vibration device structured and arranged to vibrate with predetermined vibration frequency and predetermined vibration phase in order to mechanically vibrate the body;
an emission device structured and arranged to emit in a direction of the body a coherent electromagnetic detection radiation having a radiation frequency selectable to be reflected at least in part by the body and the object to be detected;
a receiver device structured and arranged to receive the radiation reflected by the body and the object; and
an evaluation device structured and arranged to filter components at the predetermined vibration frequency from the received radiation and to evaluate the filtered components with regard to a vibration phase difference from the predetermined vibration phase.

2. The arrangement according to claim 1, wherein the arrangement is structured and arranged to carry out a security check.

3. The arrangement according to claim 1, wherein a phase difference of the filtered components from a vibration phase of the mechanical vibration of sections of the body at least one of adjacent to and surrounding the object lie in a predetermined value range.

4. The arrangement according to claim 1, wherein the object is concealed by at least one covering material, and the radiation frequency of the electromagnetic detection radiation is selected to be transmitted at least in part by the at least one covering material.

5. The arrangement according to claim 4, wherein the at least one covering material is a typical clothing material.

6. The arrangement according to claim 1, wherein the electromagnetic detection radiation is terahertz radiation.

7. The arrangement according to claim 6, wherein the electromagnetic detection radiation has a frequency between approx. 30 GHz and approx. 10 THz.

8. The arrangement according to claim 7, wherein the electromagnetic detection radiation has a frequency of between approx. 0.1 THz and approx. 1.0 THz.

9. The arrangement according to claim 1, wherein the vibration device comprises a vibration plate on which the body stands.

10. The arrangement according to claim 1, wherein the mechanical vibration has a vibration frequency in the range of between approx. 1 Hz and approx. 20,000 Hz.

11. The arrangement according to claim 1, wherein the mechanical vibration is between approx. 50 Hz and approx. 200 Hz.

12. The arrangement according to claim 1, wherein the mechanical vibration is approx. 100 Hz.

13. The arrangement according to claim 1, wherein the evaluation device comprises a superimposition device structured and arranged to superimpose a reference radiation on the received reflected radiation, in which the reference radiation is in a fixed radiation phase relationship with the detection radiation.

14. The arrangement according to claim 1, further comprising an imaging optical system with spatial resolution arranged upstream of the receiver device.

15. The arrangement according to claim 1, wherein the body is a human body.

16. The arrangement according to claim 1, wherein at least one of the radiation frequency of the detection radiation emitted by the emission device and the distance of the emission device from the body is variable.

17. A method for detecting with the apparatus according to claim 1 an object arranged on a body in a security check, the method comprising:
- acting on a body with vibration device that vibrates with predetermined vibration frequency and predetermined vibration phase in order to set the body in mechanical vibration;
- irradiating the body with a coherent electromagnetic detection radiation from the emission device having a radiation frequency selected to be reflected at least in part by the body and the object to be detected;
- receiving the radiation reflected by the body and the object with the receiver device; and
- filtering components at the predetermined vibration frequency from the received radiation and evaluating the filtered components with regard to vibration phase difference from the predetermined vibration phase in the evaluation device.

18. A method for detecting an object arranged on a body, comprising:
- acting on a body with an exciter vibration that vibrates with predetermined vibration frequency and predetermined vibration phase in order to set the body in mechanical vibration;
- irradiating the body with a coherent electromagnetic detection radiation having a radiation frequency selected to be reflected at least in part by the body and the object to be detected;
- receiving the radiation reflected by the body and the object; and
- filtering components at the predetermined vibration frequency from the received radiation and evaluating the filtered components with regard to vibration phase difference from the predetermined vibration phase.

19. The method according to claim 18 carrying out a security check.

* * * * *